United States Patent [19]

Jonsson

[11] 4,169,138

[45] Sep. 25, 1979

[54] METHOD FOR THE DETECTION OF ANTIBODIES

[75] Inventor: U. R. Svante Jonsson, Lund, Sweden

[73] Assignee: Pharmacia Diagnostics AB, Upsala, Sweden

[21] Appl. No.: 775,331

[22] Filed: Mar. 2, 1977

Related U.S. Application Data

[63] Continuation of Ser. No. 574,818, May 5, 1975, abandoned.

[30] Foreign Application Priority Data

May 29, 1974 [SE] Sweden ............................... 7407139

[51] Int. Cl.$^2$ ...................... G01N 33/16; G01N 31/06
[52] U.S. Cl. .................................. 424/12; 23/230 B; 422/57
[58] Field of Search ....................... 23/230 B, 253 TP; 424/12

[56] References Cited

U.S. PATENT DOCUMENTS

| | | | |
|---|---|---|---|
| 3,789,116 | 1/1974 | Kay | 424/12 |
| 3,904,367 | 9/1975 | Golibersuch | 424/12 |
| 3,966,898 | 6/1976 | Sjoquist | 23/230 B X |
| 4,054,646 | 10/1977 | Giaever | 23/230 B |
| 4,061,466 | 12/1977 | Sjoholm | 23/230 B |
| 4,066,744 | 1/1978 | Price | 424/12 |

OTHER PUBLICATIONS

S. Jonsson et al., Europ. Jour. of Immunology, 4, 29-33, Jan. 1974.
H. Hjelm et al., FEBS Letters, 28, 73-76, Nov. 1972.

*Primary Examiner*—Sidney Marantz
*Attorney, Agent, or Firm*—Fred Philpitt

[57] ABSTRACT

A method for the detection of antibodies immunochemically bound to the corresponding antigen fixed to a smooth surface of glass, metal, polymerfilm or the like. The surface with antigen bound antibodies is contacted with a suspension of small water-insoluble particles to which a biopolymer is directly bound, said biopolymer having the ability of binding to said antibodies, preferably at a non-antigen binding structure of the antibodies. The particles are then adsorbed only on that part of the surface where antibodies are specifically bound and the adsorbed particles forms a coating that is clearly visible by the eye.

5 Claims, No Drawings

METHOD FOR THE DETECTION OF ANTIBODIES

This is a continuation of application Ser. No. 574,818, filed May 5, 1975, abandoned.

BACKGROUND OF THE INVENTION

The present invention relates to a method for detecting the presence of antibodies in an aqueous sample, which antibodies are specifically directed to an antigen.

Several different methods are previously known for the detection of and quantitation of specific antibodies in biological samples. In one of these methods antigen-coated surfaces of glass, polymer, metal or similar materials are used. Samples possibly containing antibodies specifically directed to the antigen on the surface are applied to the surface, after which the formation of the antibody-antigen complex may be detected in different ways. Thus radioactively labelled antibodies added to the sample may compete with the antibodies in the sample and then the radioactivity specifically bound to the antigen surface is measured. The drawback with such techniques is i.a. the waste of time, the need of expensive and complicated equipment and also the risks of health when using radioactive substances.

It has also been suggested (Adams et al., Journal of Immunological Methods 3 (1973), p. 227–232) to detect the antibody-antigen complexes (1) by observing the increase of wettability upon exposure of the surface to water vapour (2) by staining with a protein dye (e.g. Coomassie Brilliant Blue R) and (3) by observing the interference colour changes on special reflecting surfaces. One common drawback with these methods is the fact that they may give unspecific reactions, as false positive reactions cannot be prevented when samples with a high protein concentration, e.g. undiluted sera, are applied. Besides, no analysis is possible of reacting specific antibodies with respect to their belonging to immunoglobulin classes, which is of a very great interest when diagnosing i.a. infection diseases.

THE PRESENT INVENTION

It has now surprisingly proved that the disadvantages in the previously used detection methods may be overcome by the present invention.

The invention relates to a method for detecting the presence of antibodies (I) in an aqueous sample, which antibodies are specifically directed to an antigen, wherein the sample is contacted with a smooth, preferably flat or tubular surface coated with said antigen for binding of the antibodies (I) to the antigen on the surface, whereupon the antibodies (I) thus bound on the surface are detected and the invention is characterized in that the surface, for the detection of the antibodies, is contacted with a suspension of small water-insoluble particles, to which a biopolymer is directly bound, which biopolymer has the ability of specific binding to antibodies, preferably belonging to a certain or certain immunoglobulin classes, and preferably at some non-antigenbinding structure of the antibodies, whereby the said particles are adsorbed on that part of the surface where the antibodies have been specifically bound to form a coating of particles that is clearly visible by the naked eye.

The term "antigen" here and in the claims also includes haptens.

The coating of antigen on the smooth surface may be obtained either by adsorptive forces or by covalent bonds between the antigen (hapten) and reactive groups on the surface, possibly by influence of bifunctional reagent. A smooth surface of glass, polymer, metal or similar material possibly coated with some substance simplifying the binding of the antigen to the surface may be used as the reaction surface. The surface may also first be coated with a layer of antibodies specifically directed to the antigen and then the antigen is adsorbed on this antibody layer. The surface may preferably be flat or tubular, alternatively formed to small cups or rods. The material of the surface may also consist of thin foils of polymer, metal or the like, if desired placed on a material of paper, polymer, glass or the like. An advantage with reaction surfaces in the form of thin foils is that they permit the storage and transport of antigen-covered surfaces, whereby the antigen may be protected from possible denaturation e.g. by a thin film of a suitable liquid. The term "coating" of antigen on the surface will here and in the claims mean that the antigen is fixed to the surface so that it cannot be dissolved from the surface at contact with the aqueous sample to the extent of disturbing the reactions.

Among the antigens that may be adsorbed or covalent bound to surfaces of glass, polymer, metal or similar material, one may specially mention polypeptide antigens including proteins, glycoproteins, lipoproteins, such as serumalbumin, immunoglobulins, other plasmaproteins including hormones of polypeptide nature, bacterial toxines and other microbial polypeptides etc.; polysaccharide antigens such as dextran, other capsule polysaccharides, lipopolysaccharides, lipopolysaccharide protein complexes from bacteria and of other origin; nucleic acids such as DNA and RNA; haptens such as small molecular hormones and drugs, if desired bound to macromolecules for improved adsorption to the surface; virus antigens such as Hepatitis B antigen (HBAg, earlier called Australia-antigen, Au-ag); particular antigens such as whole bacteria or other microbes, monocellular or polycellular parasites, animal cells or suitable (sub-) cellular fragments exemplified by whole Salmonella-, *Treponema pallidum* (syphilis-) and Chlamydia-bacteria.

The term "biopolymer" above and in the claims is preferably meant to include polypeptides, proteins, glycoproteins, polysaccharides, lipoprotein-polysaccharide complexes, no matter which part of the molecule that possesses the affinity to preferably a non-antigen-binding structure of an immunoglobulin.

The biopolymer may originate from microbes i.e. from bacteria, or have other biological origin and the biopolymer may also consist of immunoglobulins (antibodies (II)) directed to immunoglubulins (said antibodies (I)). A very suitable example of biopolymers according to the above is the so-called protein A from *Staphylococcus aureus* or fragment of said protein, which fragments are of polypeptide nature and have the ability of binding to a non-antigenbinding structure of the antibodies. Other examples of biopolymers with the corresponding qualities are a polypeptide from *Staphylococcus epidermidis* and biopolymers occuring on the surface structure of certain streptococci. The biopolymer may be bound to the surface of the microorganism which has produced it. When the biopolymer consists of protein A or fragments thereof the particles consist with great advantage of staphylococci, preferably of killed staphylococci. The preparation of a reagent of protein A-containing staphylococci may be carried out according to S. Jonsson and G. Kronvall (Eur J Immunol 4 (1974), p. 29-30), whereby a 10% suspension stable for at least one year is obtained, which when being used for detecting of IgG-antibodies, bound to an antigen on a surface, only has to be diluted to a suspension of about ½% in phosphate-buffered saline solution with addition of a suitable surfactant.

According to the invention the biopolymer may also be bound to small particles of a polymer, which is insoluble in water. Examples of such polymers are gel particles containing co-polymers of polyhydroxy-compounds and bifunctional substances e.g. the copolymer of dextran and epichlorohydrin (Sephadex®) from Pharmacia Fine Chemicals, Uppsala), gel particles containing acrylates etc. The small particles of polymers which are insoluble in water may however be swellable in water. The binding of the biopolymer to the particles may also take place by the polymerization of the biopolymer, possibly by the copolymerization with other polymers, e.g. the insolubilization of serum containing antibodies specifically directed to a certain or certain immunoglobulin classes. If desired the small particles may be stained. Particles having the size of 0.1-20, such as 0.2-10 micrometer are preferably used.

According to the invention, the biopolymer may be bound to the surface of the small particles by bonds of covalent nature or by adsorption.

According to the invention the bacteria bodies may contain in its surface layers a biopolymer originating from the same or a biopolymer with another origin. The biopolymer may be bound to the surface of the bacteria bodies by a natural linkage between the biopolymer and the bacteria bodies and/or by a linkage obtained in an artificial way. The bacteria bodies with adherent biopolymer may be treated with an aldehyde, e.g. formaldehyde and/or glutaraldehyde. They may also be treated with heat for killing and/or sterilization.

Antibodies of the IgG-class may be detected with protein A-containing staphylococci.

If antibodies that are not capable of binding to protein A are to be detected one may according to the invention use particles to which other biopolymers reacting specifically with these antibodies are directly bound.

According to another embodiment of the present invention also antibodies lacking ability of binding to protein A may be detected by exposing the antibody-antigen complex on the surface to a solution of antibodies reacting with protein A via their Fc-parts and directed to the antibodies which do not react with protein A. After that the reagent of protein A-containing staphylococci reagent is added and a possible reaction is observed in the same way as above described.

According to one further embodiment of the invention the surface with antigen bound antibodies (I) may be contacted with a suspension of bacteria bodies, to the surfaces of which antibodies (II) (via the Fc-parts thereof) directed to the said antibodies (I) are directly bound for the visualization of the surface area coated with antibodies (I).

For a semi-quantitative determination of the antibodies in a sample different techniques could be used. For example a series of different dilutions of the sample may be tested and the results may be compared with analogous tests with reference samples. The greatest dilution of the sample giving rise to a positive reaction is then established.

According to a very advantageous embodiment of the invention the presence of antibodies in a sample may be quantitatively detected by applying the sample on the surface outside the part coated with antigen and making the sample pass in one direction in one zone, preferably in a narrow zone, over the antigen coated surface. When the sample has passed, which can be observed by staining, or the like, of the sample, the suspension of the biopolymer-bearing particles is added. The surface thereby coated by these particles is a measure of the antibody content of the sample and may be related to the corresponding surface of a known reference sample.

To obtain the passage of the sample over the antigen coated surface one could use a method known in the thin layer gel-chromatography technique e.g. by applying a thin layer (or several layers besides each other) of a capillary medium e.g. of particles such as Sephadex ® G-75 Superfine (crosslinked dextran gel from Pharmacia Fine Chemicals, Uppsala). As a liquid transferring medium also threads of spun or unspun fibres may be used. Before the visualization with the biopolymer-containing particles of course said medium must first be removed.

It is also possible to obtain one linear flow of liquid or several parallel linear flows of liquid over the slide without having any support of solid material on the antigen coated surface. Then the surface first has to be wetted in a linear line or in parallel linear lines and the in-flow and out-flow of liquid to respectively from the slightly leaning slide has to be arranged by means of a suitable capillary material.

The transfer of antibodies in the sample in one direction over the antigen coated surface may also be obtained by means of an electrophoretical technique.

According to the invention antigen in a sample may be (semi)- quantitatively determined on slides coated with antibodies directed to the antigen after subsequent exposure of the slide to a second solution of specific antibody and final exposure to a suspension of reagent particles. Adherence of the particles to a surface area indicates the presence of antigen in the sample.

With the method according to the present invention the concentration of antigen in a sample may also be indirectly, semiquantitatively or quantitatively determined by testing mixtures of antigen containing samples and doses of standardized amounts of antibodies directed to this antigen and then detecting the possible excess of antibodies which have not been inhibited by the antigen in the sample.

With the method according to the present invention antibodies directed to principally different types of antigens could be detected. Thus soluble as well as insoluble (e.g. particular) antigens could be used on the surface. It is a very great advantage in relation to earlier techniques that antibodies directed to insoluble (e.g. particular) antigens could be detected in such a simple way and with a very little waste of antigen material.

The invention will be further illustrated with reference to the following working examples, which however do not limit the scope of the invention.

EXAMPLE 1

A surface of a glass slide 76×26 mm is washed in dichromic sulphuric acid, is rinsed well in water and dried with compressed air. For about 5 minutes or longer, the surface is contacted with a 1% solution of dextran (antigen) with an average molecular weight of $2 \times 10^6$ (Dextran 2000 from Pharmacia Fine Chemicals, Uppsala) in a phosphate-buffered saline solution (hereinafter called PBS and containing 0.12 M NaCl, 0.03 M phosphate, pH 7.4). Then it is rinsed well in destilled water and dried with compressed air. In order to block the uncoated parts of the glass slide the glass is then in the same way exposed to a 1% solution of a protein that is inert in the test system, e.g. serum-albumin from the same species from which the sample originates. The sample containing antibody (against dextran) is applied as 5-10 microliter drops in rows with up to 8 drops in each row by means of an automatic pipette. Dilution of samples over 1/100 shall be made in an antibody-free serum from the same species diluted to 1/100 or in a 0.1% solution of serumalbumin.

After 5-10 minutes the drops are rinsed with PBS containing 0.1% Tween ® 20 (polyoxyethylensorbitan monolaurate from Atlas Chemie G.m.b.H.) (hereinafter called T-PBS). Then the slide is put down in a horizontal position and is coated with a ½% suspension of formalin-treated and heat-killed protein A-containing staphylococci reagent (S. Jonsson, G. Kronvall, Europ J Immunol 4 (1974), p. 29) in T-PBS. After 5-10 minutes the slide is drained and rinsed with T-PBS for the elimination of the excess of the staphylococci reagent from the slide. The slide is then dipped in cuvettes containing T-PBS. The result may be observed on such wet glasses or after continued rinsing with distilled water, if desired with addition of Tween ® 20 draining on a sheet of blotting paper and air-drying. The observation is best done in obliquely transcendent light towards a dark background. A positive reaction appears as a yellow-white patch of staphylococci in an area where a test-drop had been placed; a negative reaction appears as absence of staphylococci on the surface. With this technique, a positive reaction was obtained with a rabbit anti-dextran antiserum containing 1.3 mg specific antibodies per ml, also after a dilution of 1/10,000. Human and rabbit sera may be applied undiluted without giving rise to a negative reaction.

With human sera, in which antibodies directed to dextran could be detected only with an extremely sensitive radioimmunological technique positive reactions are obtained in the actual test system also after dilutions of the sera 25 to 125 times.

Analogously IgG-antibodies from rabbit and man, respectively, directed to antigens of other chemical structures including haptens and complex, particular antigens have been detected. Examples of such antigens (antibody-combinations) which have been tested with good results are bovine serumalbumin, ovalbumin, gentamycin (an antibiotic as an example of haptens) after previous covalent binding to cyanogenbromide activated dextran 2000, Hepatitis B Antigen (HBAg, earlier called Australia-antigen, Au-ag), Salmonella-bacteria, Chlamydia-bacteria—in all cases with good correspondance to earlier used and more complicated or essentially more time-consuming methods.

EXAMPLE 2

The method of Example 1 is repeated with samples consisting of mixtures of a certain volume of solutions containing dextran in weighed amounts and a certain volume of a dilution of antibodies to dextran. This mixture has been reacted in room temperature for 5-10 minutes. The dilution of antidextran used, 1/2000 after mixture with antigen containing solution, has been chosen to give, in the absence of antigen in the sample, an evident layer of staphylococci on the surface without meaning a big excess of antibodies. Under these conditions even a minimum amount of antigen will prevent the binding of the antibodies to the antigen on the surface by reaction with the small quantity of antibodies present. This results in the absence of a layer of staphylococci as an indication of the presence of antigen. When testing the solution of known concentrations of dextran mixed with the same volumes of the above-mentioned antidextranantiserum-dilution a total inhibition of the staphylococci adsorption is obtained with a solution of antidextran having the concentration 0.1 microgram/ml and a positive staphylococci adsorption with a solution of dextran having the concentration 0.01 microgram/ml. This shows a sensitivity of this technique corresponding to that obtained in radioimmunological tests.

EXAMPLE 3

A glass slide, $20 \times 20$ cm, washed in dichromic sulphuric acid as in Example 1, is exposed to a 1% solution of bovine serumalbumin (antigen) in PBS, by the spreading of about 1 ml of the solution between 2 identical glass slides, pushed in above each other in such a way that a margin of about 3 cm is left free from antigen. Rinsing and drying is made as in Example 1, but the liquid and the air has to be blown in the direction from the antigen-free margin. All over the slide a thin layer of a gel of Sephadex ® G-75 Superfine (from Pharmacia Fine Chemicals, Uppsala, Sweden) is applied. The slide is then placed in an apparatus for so called thin-layer gel chromatography and is contacted with one upper and one lower vessel containing PBS via filter papers between which vessels liquid will flow according to the siphon principle. Samples containing antibodies (against bovine serum albumin) are applied in the form of 5-10 microliters drops of serum or dilutions thereof on the upper part of the antigen-free margin. The difference in height between the liquids is adjusted in such a way that the sample is transferred over the plate in about 3 hours. After that the gel is washed with PBS, the plate is rinsed again with T-PBS, and is then exposed to a normal rabbit serum diluted to 1/100 for about 5 minutes, is again rinsed with T-PBS and is finally exposed to the staphylococci reagent and to the rinsing fluids as in Example 1. The result is best observed in obliquely transcendent light towards a dark background as triangular areas with the basis in the borderline between the antigen surface and the margin and the apex in the flow direction of the liquid. The area is directly proportional to the amount of antibodies in the sample.

Analougously to the above technique threads of spun and unspun (so-called non-woven) fibres have been used as a support for the liquid transfer. Two advantages have then been obtained; on one hand there is no side diffusion of the sample during the transfer, on the other hand there is no need for exposing the slide to e.g. a normal rabbit serum diluted to 1/100 before the staphylococci reagent. It is also possible to achieve several parallel flows of liquid without having any support of a solid phase on the glass slide, provided that the slide is first wetted in parallel lines with e.g. wet threads and an inflow is arranged through a number of threads to the somewhat leaning slide from a vessel with its liquid surface situated about one centimeter above the upper edge of the glass slide. The outflow of liquid is arranged through threads dipped in a bath just below the lower edge of the slide. With the latter technique a more distinct ending of the surface coated with the staphylococci reagent is obtained.

I claim:

1. In the method for detecting the presence of antibodies in an aqueous sample, which antibodies are specifically directed to an antigen, whereby the sample is contacted with a smooth surface coated with said antigen for binding of antibodies to the antigen on the surface, whereupon the antibodies thus bound on the surface are detected, the improvement which comprises:

contacting said surface with a suspension of small water-insoluble particles to which a biopolymer is directly bound, said biopolymer being derived from staphylococci and being selected from the group consisting of protein A and fragments of said protein, which fragments are of polypeptide nature, and said biopolymer having the ability of specifically binding to antibodies at a non-antigen binding structure of the antibodies, whereby said particles are adsorbed on the part of the surface where antibodies are specifically bound to form a coating of particles that is clearly visible by the eye.

2. The improvement as set forth in claim 1 wherein the particles are the staphylococci bacteria bodies, which in their surface layers contain protein A.

3. The improvement as set forth in claim 1 for detecting non-protein A-reacting antibodies, wherein the surface with the antigen-bound antibodies is contacted with protein A-reacting antibodies directed to said antibodies, whereafter a suspension of protein A-containing staphylococci is added for the visualization of the surface coated with double layers of antibodies.

4. The improvement as set forth in claim 1 wherein the sample is passed in one direction in a narrow zone over the antigen-coated surface.

5. The improvement as claimed in claim 1 wherein a sample possibly containing the antigen is mixed with a known amount of antibodies directed to the antigen, whereafter the possible excess of antibodies which have not been inhibited by the antigen in the sample is detected as an indirect measure of the amount of antigen in the sample.

* * * * *